US011922330B2

(12) United States Patent
Franke et al.

(10) Patent No.: US 11,922,330 B2
(45) Date of Patent: Mar. 5, 2024

(54) APPARATUS AND METHOD FOR ESTIMATING A PHYSICAL STATE OF A MOVABLE OBJECT

(71) Applicant: Fraunhofer-Gesellschaft zur Förderung der angewandten Forschung e.V., Munich (DE)

(72) Inventors: Norbert Franke, Erlangen (DE); Sebastian Kram, Erlangen (DE); Christian Nickel, Erlangen (DE); Jochen Seitz, Erlangen (DE); Mohammad Alawieh, Erlangen (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 767 days.

(21) Appl. No.: 16/990,440

(22) Filed: Aug. 11, 2020

(65) Prior Publication Data
US 2020/0372379 A1 Nov. 26, 2020

Related U.S. Application Data

(63) Continuation of application No. PCT/EP2019/053426, filed on Feb. 12, 2019.

(30) Foreign Application Priority Data

Feb. 15, 2018 (EP) ..................... 18156982

(51) Int. Cl.
*G06F 17/18* (2006.01)
*G01C 21/28* (2006.01)
(Continued)

(52) U.S. Cl.
CPC ............... *G06N 5/04* (2013.01); *G01C 21/28* (2013.01); *G01S 19/25* (2013.01); *G01S 19/252* (2013.01);
(Continued)

(58) Field of Classification Search
CPC ........ G06N 5/04; H04W 4/029; H04W 4/027; G01C 21/28; G01S 19/25; G01S 19/252; G06F 17/18
See application file for complete search history.

(56) References Cited

U.S. PATENT DOCUMENTS

| 2002/0152035 A1* | 10/2002 | Perlin ...................... C12Q 1/68 |
| | | 702/20 |
| 2014/0163927 A1 | 6/2014 | Cole et al. |
| 2017/0064515 A1* | 3/2017 | Heikkila ............. G01S 5/02522 |

OTHER PUBLICATIONS

J. Bancroft et al., "Activity and environment classification using foot mounted navigation sensors", Indoor Positioning and Indoor Navigation (IPIN), 2012 International Conference on, IEEE, Nov. 13-15, 2012, pp. 1-10, XP032313208.

(Continued)

*Primary Examiner* — Umair Ahsan
(74) *Attorney, Agent, or Firm* — NKL Law; Jae Youn Kim

(57) ABSTRACT

An apparatus for estimating a physical state of a movable object includes a processor receiving or determining a probability mass function including probabilities for each of a first group of at least two movement classes, wherein the movement models of the first group being determined using sensor data from the inertial measurement unit. The processor receives at least one additional probability mass function associated with a second group of at least two movement classes, wherein the additional probability mass function has been obtained using additional information different from the sensor data. The processor combines the probability mass function and the at least one additional probability mass function to obtain a combined probability mass function over the movement classes of the first group and the second group, selects a movement class having the highest probability from the combined probability mass function, (Continued)

and estimates the physical state of the movable object using a movement model of the selected movement class. Each movement class is either a movement state or a movement model.

17 Claims, 10 Drawing Sheets

(51) Int. Cl.
    *G01S 19/25*     (2010.01)
    *G06N 5/04*     (2023.01)
    *H04W 4/02*     (2018.01)
    *H04W 4/029*     (2018.01)

(52) U.S. Cl.
    CPC ............ *G06F 17/18* (2013.01); *H04W 4/027* (2013.01); *H04W 4/029* (2018.02)

(56) References Cited

OTHER PUBLICATIONS

Christian Eiltner, "Office Action for EP Application No. 19703738.5", dated Dec. 16, 2021, EPO, Netherland.
Wikipedia—Type Allocation Code, URL: https://en.wikipedia.org/wiki/Type_Allocation_Code.
IMEI Check—Free Online IMEI Number Checker, URL: http://www.imei.info.
3GPP TSG RAN WG2#100, Reply LS on Certification/License and Identification of Aerial Vehicles, Rel. 15, R2-1712152.
3GPP TS 36.331 V16.1.1 (Jul. 2020), E-UTRA, RRC, Protocol Specification, Release 16.

* cited by examiner

APPARATUS AND METHOD FOR ESTIMATING A PHYSICAL STATE OF A MOVABLE OBJECT

CROSS-REFERENCES TO RELATED APPLICATIONS

This application is a continuation of copending International Application No. PCT/EP2019/053426, filed Feb. 12, 2019, which is incorporated herein by reference in its entirety, and additionally claims priority from European Application No. EP 18 156 982.3, filed Feb. 15, 2018, which is incorporated herein by reference in its entirety.

BACKGROUND OF THE INVENTION

The present disclosure relates to apparatuses and methods for estimating a physical state of a movable object.

In the context of modern mobile radio standards, classification and transmission of movement states play an important role. Generally, it is known to perform classification of movement states by evaluating sensor data obtained from an inertial measurement unit (IMU), for example. Examples of movement states are pedestrian specific movement states such as walking, jogging, running or sprinting, and vehicle specific movement states, such as driving or standing in a traffic jam. Generally, a movement state defines the state in which a movable object is. After classifying the movement state, a movement model associated with the movement state may be selected. The movement model is modelling the behavior of the sensor data, from which the movement state is classified, in the respective movement state. Using the movement model and the sensor data obtained from the IMU, a physical state of a movable object, such as a mobile phone, may be estimated using the sensor data and the selected movement model.

SUMMARY

An embodiment may have an apparatus for estimating a physical state of a movable object, the apparatus including a processor, wherein the processor is configured to receive or determine a probability mass function including probabilities for each movement class of a first group of at least two movement classes, wherein the movement classes of the first group being determined using sensor data from the inertial measurement unit, receive at least one additional probability mass function associated with a second group of at least two movement classes, wherein the additional probability mass function has been obtained using additional information different from the sensor data; combine the probability mass function and the at least one additional probability mass function to obtain a combined probability mass function over the movement classes of the first group and the second group; select a movement class having the highest probability from the combined probability mass function; and estimate the physical state of the movable object using a movement model of the selected movement class, wherein each movement class is either a movement state or a movement model.

Another embodiment may have an apparatus for estimating a physical state of a movable object, the apparatus including a processor, wherein the processor is configured to receive at least one probability mass function including probabilities for each movement class of a group of at least two movement classes, wherein the probability mass function is based on information from an information source; receive a quality measure for the probability mass function, the quality measure indicating a quality of the information source; select a movement class having the highest probability from the at least one probability mass function, and estimate the physical state of the movable object using a movement model of the selected movement class and the received quality measure, wherein each movement class is either a movement state or a movement model.

Another embodiment may have a system including the inventive apparatuses and at least one information source, wherein the at least one information source is configured to transmit the probability mass function, the additional probability mass function or the at least one additional probability mass function to the apparatus.

Another embodiment may have a method for estimating a physical state of a movable object, the movable object including an inertial measurement unit, the method including: receiving a probability mass function including probabilities for each movement class of a first group of at least two movement classes, wherein the movement classes of the first group being determined using sensor data from the inertial measurement unit; receiving at least one additional probability mass function associated with a second group of at least two movement classes, wherein the additional probability mass function has been obtained using additional information different from the sensor data; combining the probability mass function and the additional probability mass function to obtain a combined probability mass function over the movement classes of the first group and the second group; selecting a movement class having the highest probability from the combined probability mass function; and estimating the physical state of the movable object using a movement model of the selected movement class, wherein each movement class is either a movement state or a movement model.

Another embodiment may have a method for estimating a physical state of a movable object, the method including: receiving at least one probability mass function comprising probabilities associated with a group of at least two movement classes, wherein the probability mass function is based on information from an information source; selecting a movement class having the highest probability from the at least one probability mass function; receiving a quality measure for the probability mass function, the quality measure indicating a quality of the information source; and estimating the physical state of the movable object using a movement model of the selected moving class and the received quality measure, wherein each movement class is either a movement state or a movement model.

Another embodiment may have a non-transitory computer program product including a computer readable medium storing instructions which, when executed on a computer, perform the inventive methods.

Examples of the present disclosure provide an apparatus for estimating a physical state of a movable object, comprising a processor. The processor is configured to receive or determine a probability mass function including probabilities for each of a first group of at least two movement classes, wherein the movement classes of the first group being determined using sensor data from the inertial measurement unit, and to receive at least one additional probability mass function associated with a second group of at least two movement classes, wherein the additional probability mass function has been obtained using additional information different from the sensor data. The processor is configured to combine the probability mass function and the additional probability mass function to obtain a combined probability mass function over the movement classes of the first group and the second group. The processor is further configured to select a movement class having the highest probability from the combined probability mass function, and to estimate the physical state of the movable object using a movement model of the selected movement class.

Examples of the present disclosure provide a method for estimating a physical state of a movable object, the movable object comprising an inertial measurement unit, the method comprising: receiving a probability mass function including probabilities for each of a first group of at least two movement classes, wherein the movement classes of the first group being determined using sensor data from the inertial measurement unit; receiving at least one additional probability mass function associated with a second group of at least two movement classes, wherein the additional probability mass function has been obtained using additional information different from the sensor data; combining the probability mass function and the additional probability mass function to obtain a combined probability mass function over the movement classes of the first group and the second group; selecting a movement class having the highest probability from the combined probability mass function; and estimating the physical state of the movable object using a movement model of the selected movement class.

Thus, in examples of the present disclosure, information from additional information sources that may be present in a linked system and that may give a hint to a physical state, such as a movement state, of a movable object, may be used in order to select a movement model to be used in estimating the physical state of the movable object, such as a mobile phone.

Examples of the present disclosure provide an apparatus for estimating a physical state of a movable object, comprising a processor which is configured to receive at least one probability mass function comprising probabilities associated with a group of at least two movement classes, wherein the probability mass function is based on information from an information source, and to receive a quality measure for the probability mass function, the quality measure indicating a quality of the information source. The processor is configured to select a movement class having the highest probability from the at least one probability mass function, and to estimate the physical state of the movable object using a movement model of the selected movement class and the received quality measure.

Examples of the present disclosure provide a method for estimating a physical state of a movable object, the method comprising: receiving at least one probability mass function comprising probabilities associated with a group of at least two movement classes, wherein the probability mass function is based on information from an information source; selecting a movement class having the highest probability from the at least one probability mass function; receiving a quality measure for the probability mass function, the quality measure indicating a quality of the information source; and estimating the physical state of the movable object using a movement model associated with the selected movement class and the received quality measure.

Thus, in examples of the present disclosure an additional quality measure is used in estimating the physical state of the movable object, such that it is possible to reliably estimate the physical state with a low variance if the quality measure indicates a high quality, while the physical state is estimated with a higher variance if the quality measure indicates a low quality. Thus, examples of the present disclosure permit outputting the physical state with an accuracy which depends on the quality measure.

Each movement class may either be a movement state or a movement model. In other words, in examples, each movement class is a movement state which has associated therewith one or more movement models, wherein the movement model or one of the movement models associated with the movement state is used in estimating the physical state of the movable object. In other examples, each movement state is the movement model used in estimating the physical state of the movable object itself, such as if there is a one to one correspondence between movement states and movement models.

DETAILED DESCRIPTION OF THE INVENTION

In the following, embodiments of the present invention are described in further detail with reference to the enclosed drawings in which elements having the same or similar function are referenced by the same reference signs.

Examples of the present disclosure may be provided in a mobile radio system, such as 3GPP systems, for example LTE systems or 5G systems, in order to improve localization of a mobile object using movement models. Beside sensor data captured by the mobile object, such as IMU data, additional information sources may be involved in the classification of movement states, i.e. the allocation of the captured data to one or more movement states.

Generally, movement states and movement models are known in the art. Movement states describe states which the mobile object is in. For example, possible movement states are pedestrian specific movement states, such as creeping, walking, running or sprinting, and vehicle specific movement states, such as driving or standing in a traffic jam. Each movement state may have associated therewith one movement model or several movement models. A movement model is modelling the behavior of the sensor data or other information, from which the movement state is classified, in the respective movement state. Using such movement models in addition to sensor data captured by the movable object may improve the accuracy and reliability of the estimation of a physical state of the movable object. The physical state of the object may be at least one of the position(s) of the object, the orientation of the object, the moving speed of the object, the rotary speed of the object, and the acceleration of the object, as well as derivations of these parameters in time. Movable objects may be any objects that are configured to communicate within a communications network, such as a 3GPP network, for example a LTE or a 5G network. Movable objects may be any mobile objects that are suitable for IOT (internet of things).

Generally, it is known how movement models can be used in connection with the sensor data captured by the mobile device to estimate the physical state of the movable object. Examples of the present disclosure relate to an approach for improving classification of the sensor data in a specific movement class, i.e. in a movement state or a movement model.

Figure 1:
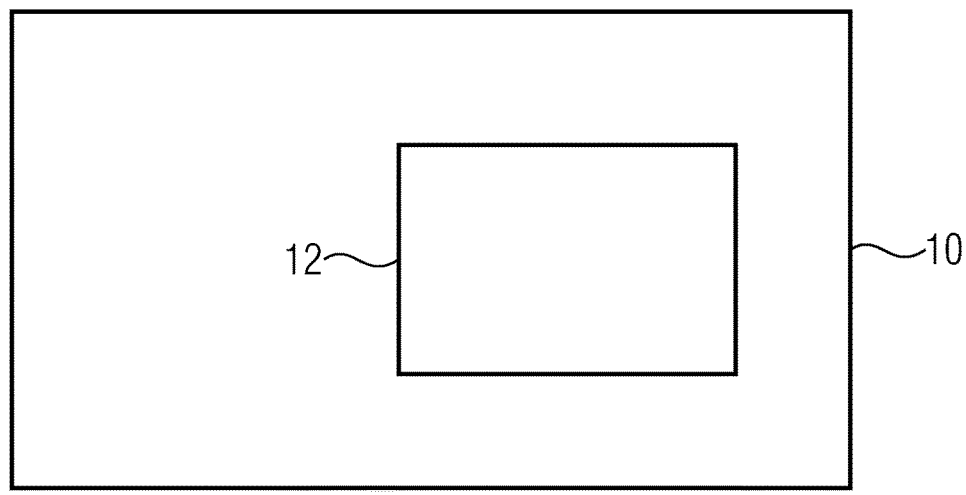
FIG. 1 shows a schematic view of an apparatus according to an example of the present disclosure.

FIG. 1 shows an apparatus 10 comprising a processor 12. The processor 12 is configured to provide the functionality described herein. The processor may be implemented as a part of the movable object or may be implemented as a separate entity, such as a location server.

The processor 12 may be implemented in hardware using analog and/or digital circuits, in software, through the execution of instructions by one or more general purpose or special-purpose processors, or as a combination of hardware and software. For example, embodiments of the present invention may be implemented in the environment of a computer system or another processing system. The apparatus 10 may be in the form of a computer system including one or more processors, like a special purpose or a general purpose digital signal processor. The processor may be connected to a communication infrastructure, like a bus or a network. The computer system may include a main memory, e.g., a random access memory (RAM), and a secondary memory, e.g., a hard disk drive and/or a removable storage drive. The secondary memory may allow computer programs or other instructions to be loaded into the computer system. The computer system may further include one or more communications interfaces to allow software and data to be transferred between components of the computer system and between the computer system and external devices. The communication may be in the form electronic, electromagnetic, optical, or other signals capable of being handled by a communications interface. The communication may use a wire or a cable, fiber optics, a phone line, a cellular phone link, an RF link and other communications channels.

In examples, the processor 12 may receive the respective information and data via the communications interface.

Figure 2:
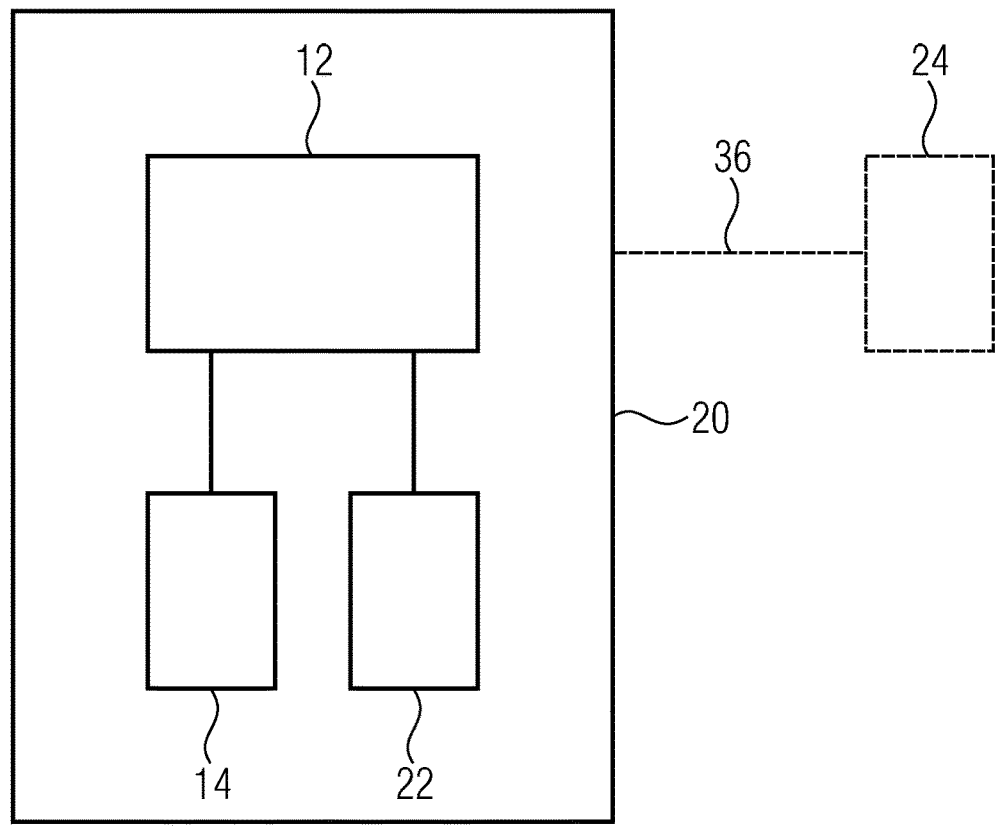
FIG. 2 shows a schematic view of an apparatus according to an example of the present disclosure.

FIG. 2 shows an apparatus 20 comprising the processor 10 and a communications interface 14. The apparatus further comprises a sensor unit 22, such as an IMU. The processor 12 may receive sensor data form the sensor unit 22 and may determine a probability mass function including probabilities for each of a first group of at least two movement classes from the sensor data. Alternatively, the processor may receive the probability mass function via the communications interface 14. The processor 12 may further receive at least one additional probability mass function associated with a second group of at least two movement classes via the communications interface 14.

The processor 12 combines the probability mass function which is based on the sensor data and the additional probability mass function to obtain a combined probability mass function. The processor 10 selects a movement class having the highest probability from the combined probability mass function and estimates the physical state of the movable object using movement model of the selected movement class. If the movement class is a movement state, a movement model associated with the movement state will be selected. Otherwise, the movement class already indicates the movement model to be used.

Examples of the present disclosure provide a fusion or combination of probability mass functions associated with different information. As it is described herein, different types of information, which may stem from different components (information sources) within a linked system, such as an IOT system, may be used in estimating a physical state of a movable object. Examples of the present disclosure provide an information fusion approach so that the best possible information about the physical state (movement state) may be available to all members of the linked system.

Examples of the present disclosure provide a system comprising an apparatus as described herein and at least one information source, wherein the at least one information source is configured to transmit a probability mass function associated with the information source to the apparatus, such as over a radio communication link. FIG. 2 schematically shows an information source 24 coupled to the apparatus 20 via a radio communication link 26. In examples, a plurality of information sources may be coupled to the apparatus via respective radio communication links. Each information source may transmit the associated probability mass function to the apparatus.

The apparatus may be implemented in the user equipment associated with the movable object, such as a mobile phone, or may be implemented as a separate entity, such as a location server. When implemented in the movable object, the apparatus may determine the probability mass function based on sensor data captured by the mobile object and may receive the additional probability mass function via a radio communication link. When implemented as a separate entity, the apparatus may receive all probability mass functions via a radio communication link.

Figure 3:
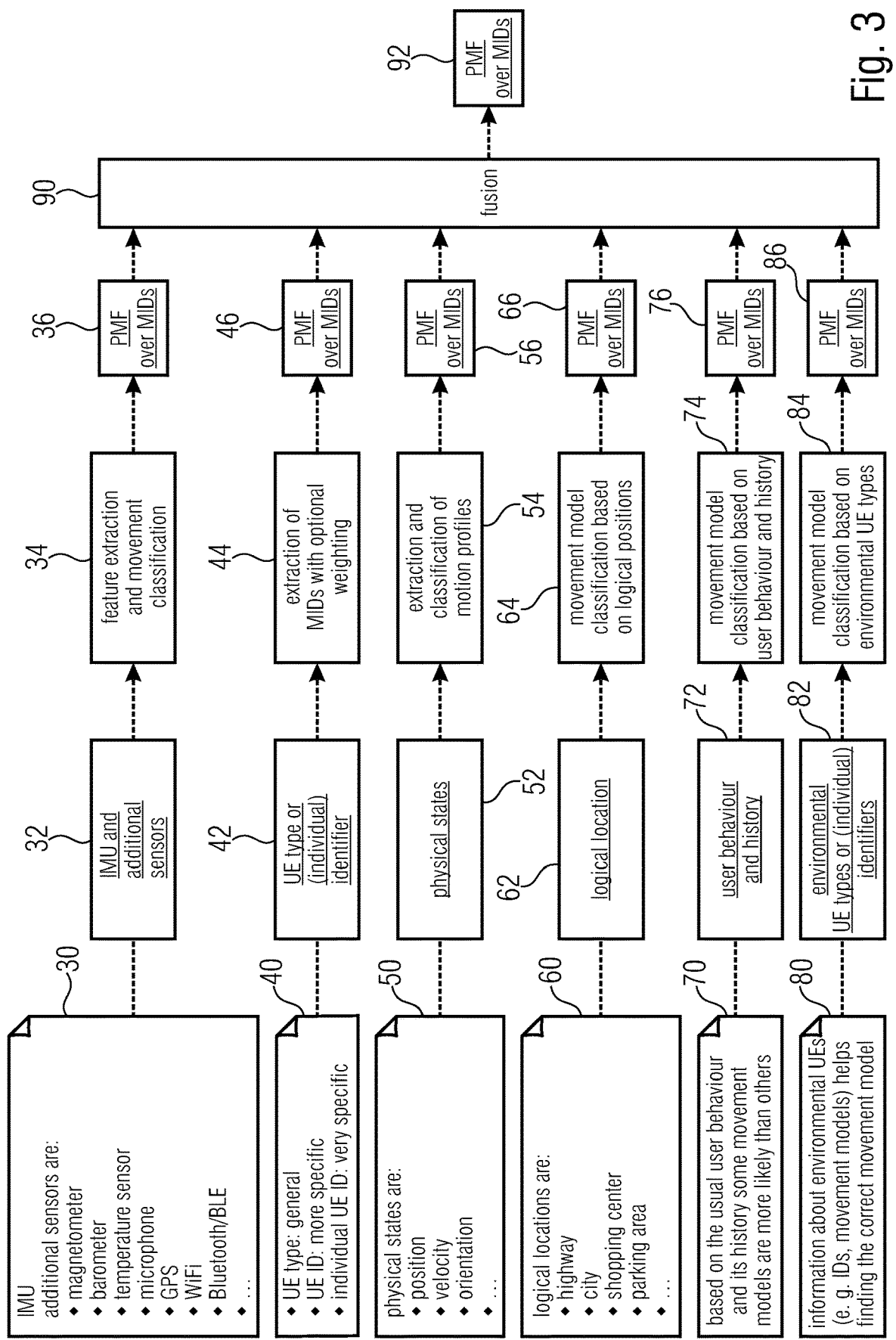
FIG. 3 shows a schematic diagram of an apparatus according to an example of the present disclosure.

FIG. 3 shows a schematic view for explaining examples of the inventive approach and different types of information and the relation thereof with respect to the physical state of the movable object will be explained.

Different types of information, which may stem from different components of a linked system, are shown in FIG. 3. The most important information is shown in block 30 and concerns IMU sensor data, such as three-dimensional IMU sensor data. Optionally, the information may include additional information, such as information stemming from a magnetometer, a barometer, a temperature sensor, a microphone, a GPS receiver, a wireless local area network receiver, and a Bluetooth receiver. The information 30 stems from sensors or devices on the movable object itself and, therefore, is captured by the movable object itself.

Data 32 representing the information 30 are provided and feature extraction and movement classification takes place in a block 34. Different approaches for feature extraction and classification are known. The result is a group of movement classes (MIDs) best fitting to the features extracted from data 32. Each selected movement class is provided with a probability and a probability mass function (PMF) over the selected movement classes is determined, block 36. The probability associated with each class may depend on the conformity between the extracted features and the respective movement class.

Block 40 shows represents another type of information relating to the identity of the mobile object, which may also be referred to as a user equipment (UE). Three detail ranks are shown in block 40, i.e. UE type, UE ID and Individual UE ID. Data 42 relating to the information 40 are provided and an extraction of fitting movement classes (MIDs) 44 takes place. In extracting fitting movement classes, an optional weighting may take place. A probability is associated with each MID and a corresponding PMF over the MIDs is provided, block 46.

The most general rank of the information 40 is the UE type indicating the type of the object, such as a car or a mobile phone. The type of the object may limit the movement state with which the object moves or is moved hardly. For example, a car may not move like a pedestrian so that pedestrian specific models, such as walking, jogging, etc., may be excluded from the beginning and need not be evaluated. Such a limitation may result in a group of possible movement classes which may be weighted according to the expected occurrence probability (a-priori probability). For example, a mobile phone will be carried by a pedestrian walking on a street more often than by a pedestrian located on a ship.

A more specific information is the UE ID in block 40. The UE ID is used in this context to refer to a specific device, rather than the individual device. An example would be the ID of a specific UE type radio module used in all cars of a specific type, such as an Audi® A8, construction year 2017 with a specific configuration. This ID may give additional information on the quality to be expected for the movement state classification (since information of the number and quality of the sensors of the device are available when knowing his ID).

The most specific information in in block 40 is the ID identifying an individual device (UE). Such an ID may be assigned to the UE or may be an existing ID, such as a MAC address, a serial number, a device ID or the International mobile equipment identity (IMEI) of each mobile device. Many objects and, thus, the information generated by each device coupled to the object, often move in accordance with a specific pattern. This movement behavior may also be involved in the classification. For example, if it is known that a user of mobile phone A is jogging on a regular base, while a user of mobile phone B is cycling frequently, a speed of 10 km/h would suggest "jogging" in case of the user of mobile phone A and would suggest "cycling" in case of the user of mobile phone B.

The information indicated above may be considered in the probabilities associated with the MIDs in block 46.

Block 50 shows additional information in the form of physical states of the object. The physical states may be derived from sensor data obtained by sensors on the object or from sensor data obtained by external sensors. Data 52 indicating the physical states, such as position and speed, are provided and a feature extraction and classification of movement classes (movement profiles) takes place, block 54. A PMF over the MIDs resulting from the classification is provided, block 56. The information on the physical states may influence the PMF. For example, it is unlikely that the user of a mobile phone is on the way by foot if he moves with a speed of 50 km/h or if is 400 m above ground.

Another type of information, i.e. logical locations, are indicated in block 60. Logical locations do not represent an absolute position but the environment in which the object is located. Examples for logical positions are a highway, a city, a shopping center, a parking area, etc. Information on the logical location may be determined by referring to map information. The logical location may include useful information since it may further limit the possible moving states. For example, the user of a mobile phone will not be moving by car if he is in a shopping center. On the other hand, it will be likely that the user will be moving by car if the logical location is a highway.

Another type of information, i.e. the usual user behavior and its history are indicated in block 70. Based on such information, some movement classes are more likely than others and this may be reflected in the PMF associated with the MIDs extracted based on this information. This type of information may be used in connection with the information in block 40 so that a UE can be identified to use the history.

Block 80 shows a further type of information, i.e. information from other devices in the vicinity of the object. Information from such devices may be used to make a context to thus support the estimation of the own movement state. For example, in the mobile radio standards, such as the 5G standard, there is the possibility that data are exchanged locally directly between several devices (UEs) by means of D2D (device to device) or via a Location Server (LS). Thus, information on how many devices of the same type are nearby and on the actual movement state thereof may be available. Such information may be useful to verify specific conditions, such as the fact that a vehicle is in a traffic jam.

As shown in FIG. 3 in blocks 62 to 66, 72 to 76 and 82 to 86, a respective PMF over the MIDs associated with the respective information 60, 70 and 80 may be provided in a similar manner as described above with respect to the information in blocks 30, 40 and 50.

According to examples of the present disclosure, one or more of the different types of information 40 to 80 described above referring to FIG. 3 may be used in finding an appropriate movement class, in addition to the information 30 stemming from one more sensors of the object.

Each combination of blocks 30 to 36, blocks 40 to 46, blocks 50 to 56, blocks 60 to 66, blocks 70 to 76, and 80 to 86, may be part of a respective information source that is configured to transmit the respective PMF to an apparatus as described herein, which is configured to combine the received PMFs, to select a movement class based on the combined PMF and to estimate the physical state of the movable object using a movement model associated with the selected movement class.

According to examples of the present disclosure, the information on the movement state is represented in a form that, on the one hand, permits weighting of the probabilities of different movement models from one information source and, on the other hand, permits weighting of the information sources relative to each other. Thus, combination or fusion of the different information sources is possible in an efficient manner, rather than presenting a hard decision, such as UE A is moved with movement model MID4. Thus, according to examples of the present disclosure, the possible fitting movement classes are represented in the form of a PMF, wherein a probability value $p_{MIDi}$ is associated with each movement class that has been determined as a possibly fitting movement class, wherein i represents an index of 1 to n and n is the number of possible movement classes. As described above, the number of movement states of a UE can typically be limited in view of the different types of information described.

The following table shows the representation of the PMF over the MIDs from 1 to n (for a number of n possible movement classes, for example movement states).

| MID1 | MID2 | ... | MIDn |
|------|------|-----|------|
| P$_{MID1}$ | P$_{MID2}$ | ... | P$_{MIDn}$ |

In examples, corresponding PMFs are transmitted between different entities of a network. In examples, MID1 to MIDn indicate different movement states. In examples MID1 to MIDn indicated different movement models. For example, MID1 to MIDn may indicate different movement models in case there is a one-to-one correspondence between a respective movement state and an associated movement model.

The probability mass function itself includes a hint as to the quality of the estimation which may stem from the source of the information itself. The closer the probability mass function is to a uniform distribution, the less sure the information source is. For example, in case of two possible movement states, the information source would be completely unsure if a probability of 50% is associated with both states, while the information source would be completely sure if a probability of 100% is associated with one of the movement class and a probability of 0% is associated with the other movement class.

By combining the probability mass functions stemming from different information sources, and selecting a movement class based on the combined probability mass function, the appropriate movement class and, thus, movement model, can be selected with increased reliability. The combination (or fusion) of the probability mass functions is indicated in FIG. 3 in block 90. The result of the combination is a combined probability mass function 92.

The PMFs to be combined may comprise the same movement classes or different movement classes.

In examples, PMFs over movement classes are transmitted between different information sources or at least between information sources and an apparatus in which the physical state of the movable object is estimated. In examples, the number of transmitted probabilities of movement classes is limited, wherein the probabilities of unlikely states, i.e. movement classes, are not transmitted. In examples, PMFs over a specific number of the most likely movement classes are transmitted only, such as a number of three PMFs.

In examples of the present disclosure, the combination of the probability mass functions is performed by calculating a weighted normalized sum of the probability mass functions.

In examples of the present disclosure, a quality measure indicating a quality of the information source which the PMF stems from, may be provided for at least one of the information sources. The quality measure may be in the form of a weighting factor, wherein the weighting factor is applied to all probabilities in the PMF in the same manner. Thus, it is possible to provide an assessment of the reliability of the information sources that is taken into consideration in selecting the appropriate movement class (state). Different from the PMF, the quality measure may describe how the overall system rates the information source. Thus, information sources which cannot contribute much to the decision between different movement states may be prevented from being weighted to high. Generally, the PMF of an information source rated as being more reliable should be weighted higher than an information source rated as being less reliable.

There are multiple possibilities to represent quality measures for states obtained by movement models and or IMU data: 1. The simplest way may be to send a device identifier. From the type of device (e.g. specific smartphone model), an assumption can be made in terms of the expected quality. This option will cause the least amount of traffic, but is probably not very accurate. 2. A better option from a sensor fusion point of view is the calculation of a variance of the states (i.e. the expected quadratic deviation from the estimate).

It may prepare a Location Server for the fusion of multiple information sources, but because the measure may be calculated on the UE, it is not controllable in how this variance is calculated. Some UEs could over- or underestimate their reliability. 3. Another option is to transmit information about the (IMU and/or additional) sensors/information sources used in obtaining the state. The package would contain type and quality of used sensors. If the used movement model is also transmitted, it can give additional information about the expected quality.

In an example of the present disclosure, the UE type of the movable object concerned is transmitted to all information sources that can generate movement state estimates, limiting the possible movement states. The information sources estimate the movement states and represent their results in a PMF. The PMFs for all movement states may be limited to the N (e.g. 3) most likely estimates. The PMF may be renormalized so that the sum of all probabilities is one again. The information source may be assigned a quality measure $\sigma_i$ (either from an external device, such as a location server, or by itself). The PMFs created by the information sources may be linked into a general (combined) PMF using a normalized weighted sum (the PMFs corresponding to states excluded in transmission can be set to 0). Thus, for M information sources, the combined PMF may be obtained as:

$$PDF_{ALL} = \frac{\sum_{i=1}^{M} \frac{1}{\sigma_i} PDF_i}{\sum_{i=1}^{M} \frac{1}{\sigma_i}}$$

In examples of the present disclosure, a quality measure for a single probability mass function is received and the physical state of the movable object is estimated using a movement model of the movement class of the single probability mass function, which has the highest probability and the received quality measure.

Such examples may not comprise a fusion of several PMFs. The single probability mass function may be based on information from an inertial measurement unit. Such examples may estimate the physical state to reveal a variance of the physical state, wherein the variance depends on the quality measure, wherein a larger variance is achieved for a lower quality measure and a smaller variance is achieved for higher quality measures. In such examples, a plurality of probability mass functions may be received, each comprising probabilities associated with a group of at least two movement models. Each probability mass function may be based on information from a different information source. A quality measure may be received for one or more of the probability mass functions. The probability mass functions may be combined using the one or more quality measures such that a probability mass function having a higher quality is weighted higher than a probability mass function having a lower quality to obtain a combined probability mass function. The movement class having the highest probability may be selected from the combined probability mass function.

Figure 4:
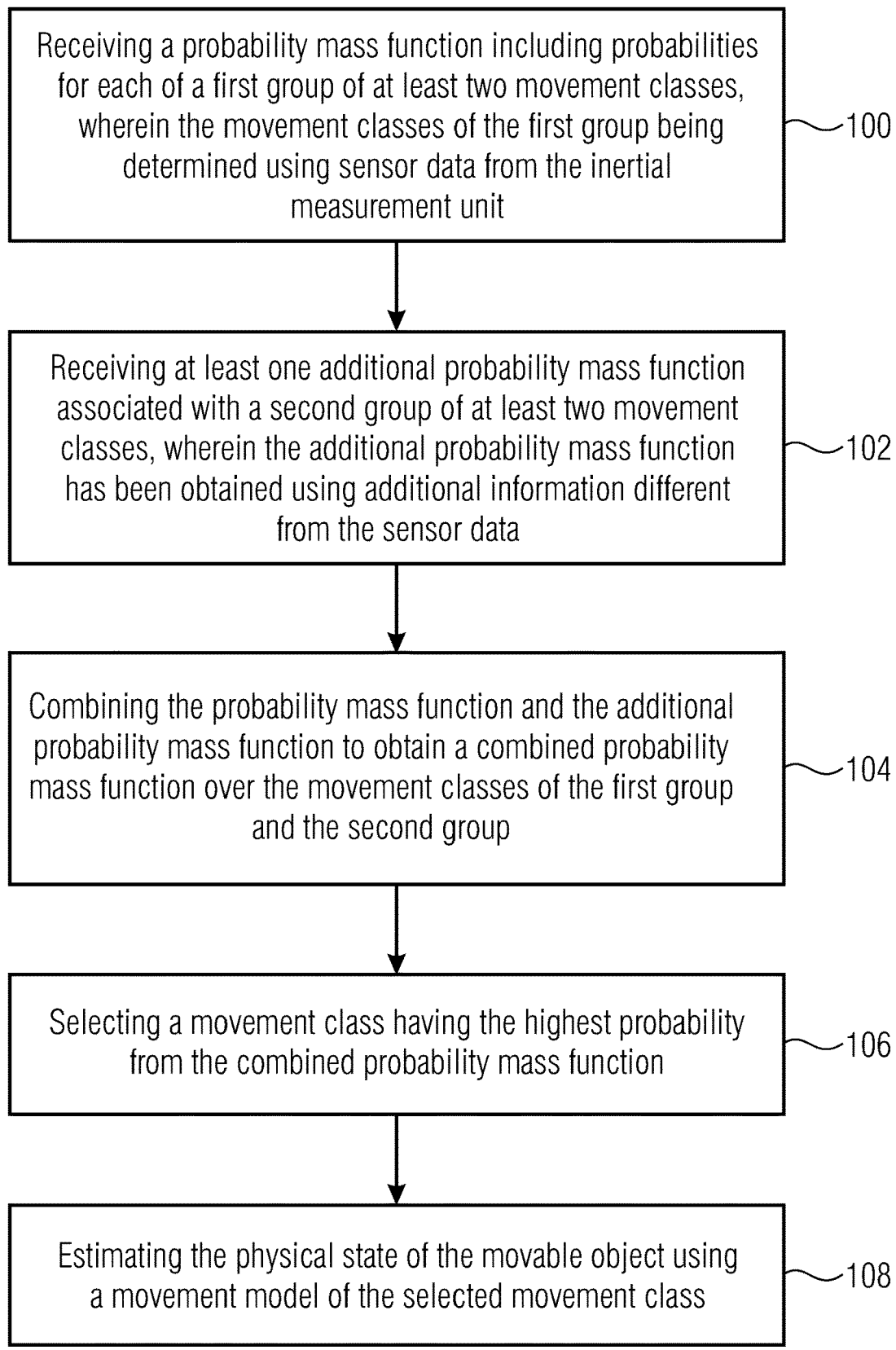
FIG. 4 shows a schematic flow chart of a method according to an example of the present disclosure.

Examples of the present disclosure provide a method for estimating a physical state of a movable object having an inertial measurement unit as shown in FIG. 4. At 100, a probability mass function including probabilities for each of a first group of at least two movement classes is received, wherein the movement classes of the first group being determined using sensor data from the inertial measurement unit. At 102, at least one additional probability mass function associated with a second group of at least two movement classes is received, wherein the additional probability mass function has been obtained using additional information different from the sensor data. At 104, the probability mass function and the additional probability mass function are combined to obtain a combined probability mass function over the movement classes of the first group and the second group. At 106, a movement class having the highest probability is selected from the combined probability mass function. At 108, the physical state of the movable object is estimated using a movement model of the selected movement class.

Figure 5:
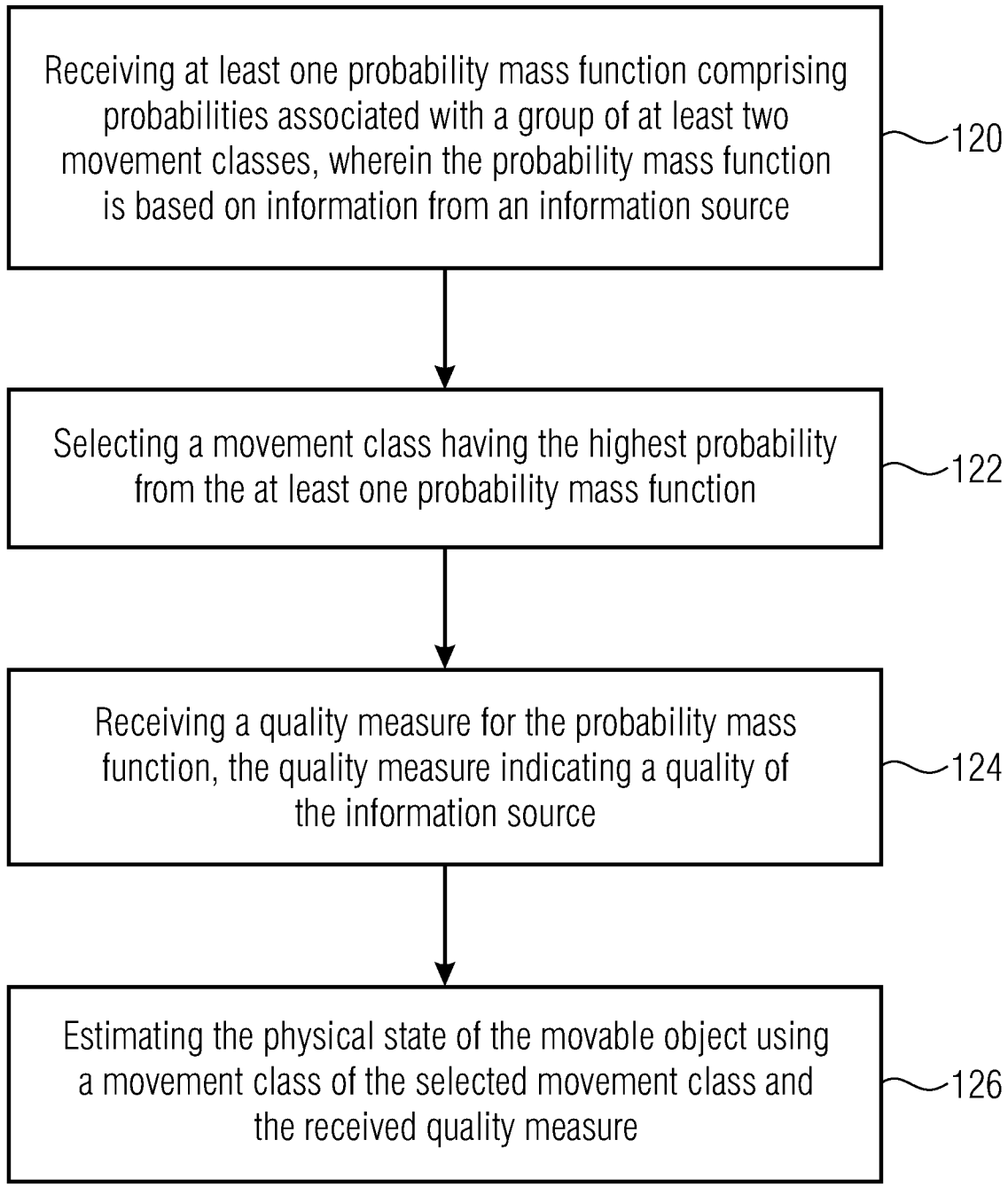
FIG. 5 shows a schematic flow chart of a method according to another example of the present disclosure.

Other examples of the present disclosure provide a method for estimating a physical state of a movable object as shown in FIG. 5. At 120, at least one probability mass function comprising probabilities associated with a group of at least two movement classes is received, wherein the probability mass function is based on information from an information source. At 122, a movement class having the highest probability is selected from the at least one probability mass function. At 124, a quality measure for the probability mass function is received, the quality measure indicating a quality of the information source. At 126, the physical state of the movable object is estimated using a movement model of the selected movement class and the received quality measure.

Figure 6:
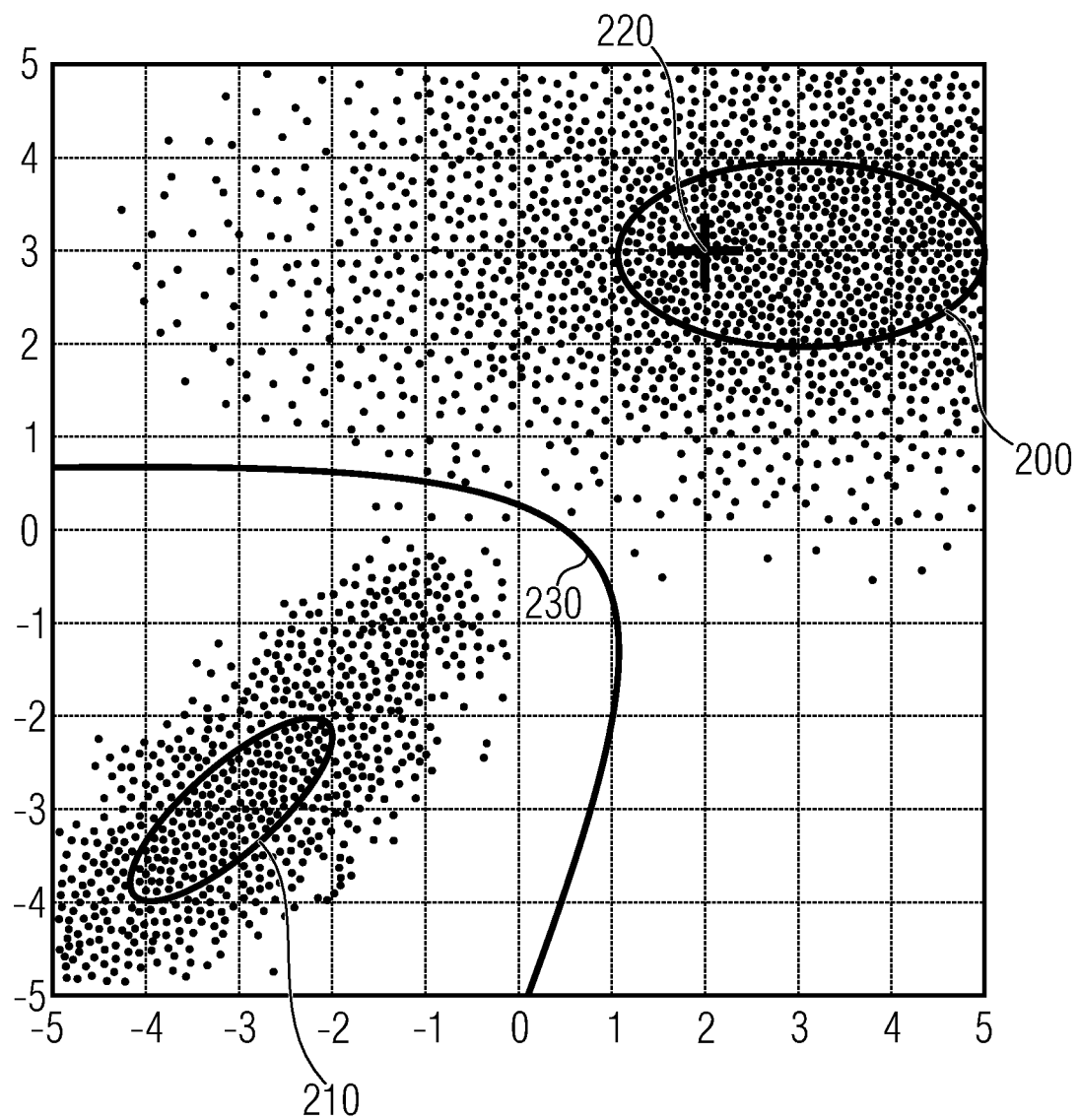
FIG. 6 shows a schematic diagram for explaining an example for associating measured data to one of more movement models.

A short example as to how classification could take place based on a feature vector is now described referring to FIG. 6. Generally, the purpose of classification is to assign measured data, which may be in the form of a multidimensional feature vector, to a class, i.e. a movement class, such as a movement state, in the present disclosure. For example, a Gaussian distribution may be assigned to a class, which corresponds to an expected distribution of the feature vectors associated with this class. The expected distribution may be determined by data or in any other manner. FIG. 6 shows to classes, wherein a first class 200 and a second class 210 are shown as clusters of spots. The Gaussian distributions are shown as ellipses representing the 95% percentiles. In addition, the classes are weighted with an a-priori probability indicating the probability that class is present at all. If a feature vector, such as [3,2] indicated by a cross 220 is measured, a class $C_x$ is associated with the feature vector, at which the probability that the spot is generated by this Gaussian distribution $p(x\backslash C)$ (that is, in the example the value which the Gaussian distributions of classes at the position x have) multiplied by the a-priory probability $p(C)$ of the class is highest:

$$C_x = \underset{C}{\mathrm{argmax}} p(C) p(x \mid C).$$

By means of normalization, the probabilities for each class may be obtained. In FIG. 6, a separating line 230 between both classes is shown. On this separating line both classes have the same probability. In the direction of the respective ellipse, the probability that the feature vector belongs to the associated class increases. Thus, in FIG. 6, the probability that feature vector 220 belongs to class 200 is much higher than the probability that feature vector 220 belongs to class 210

As will become apparent from the subsequent considerations, the use of specific movement models for different navigation scenarios has been proven to be advantageous. In addition to providing valuable information for the prediction step for navigation algorithms like Bayes filters typically used in navigation, the movement state itself contains valuable information, as it defines the role of the UE (or, more precisely, the movable object it is carried by) in a traffic scenario. These benefits will be highlighted in the following.

The role of movement models in navigation is to provide an estimate of a physical state, such as the position of the tracked object that can be compared with a measurement. As an example to show the positive effect of movement modelling, an object moving in 1-dimensional space is observed at a time index t, with a previous position estimate from an earlier time step present. The time between the time steps is τ=1 s. At time index t, the object has the position $p_t$. The measurement me is the position $p_t$ but is perturbed by the noise process $n_t$ $$m_t = p_t + n_t.$$

In an example case, the true position $p_t$ is 2.1 m, while the noise equates to another 0.4 m, so that the measurement m would indicate a position of $p_t$=2.5 m. But information from the last time step t−1 has been calculated and can be used:

$$p_{t-1} = 1m$$

$$v_{t-1} = 1m/s$$

Under the assumption that the object moves with a constant velocity in this time step (which is the movement model in this simplified example), the following prediction of the position can be made:

$$\hat{p}_{t|t-1} = p_{t-1} + \tau v_{t-1} = 2.0m$$

Now, the measurement and the prediction both carry valuable information, but the truth lies "in between". If both sources of information are valued the same, the estimate is:

$$\hat{p}_{t|t} = \frac{\hat{p}_{t|t-1} + m_t}{2} = 2.25 \text{ m},$$

which is much closer to the original position.

If, however, both the measurement and the movement model can be further described with a reliability measure (which, in most cases is a variance or covariance matrix), the result can be further improved. For the example these measures are converted into weights so that the information from the prediction is assumed to be twice as reliable as the measurement, because the noise is rather strong and the velocity of the object is almost constant in-between time steps. The resulting estimate is $$\hat{p}_{t|t} = \frac{2\hat{p}_{t|t-1} + 1\ m_t}{3} = 2.167 \text{ m}$$

which is even closer to the true position.

This simple example shows that using a quality measure for the probability mass function in estimating the physical state of the movable object may have a positive effect on the accuracy of the estimated position of the movable object.

Figure 7:
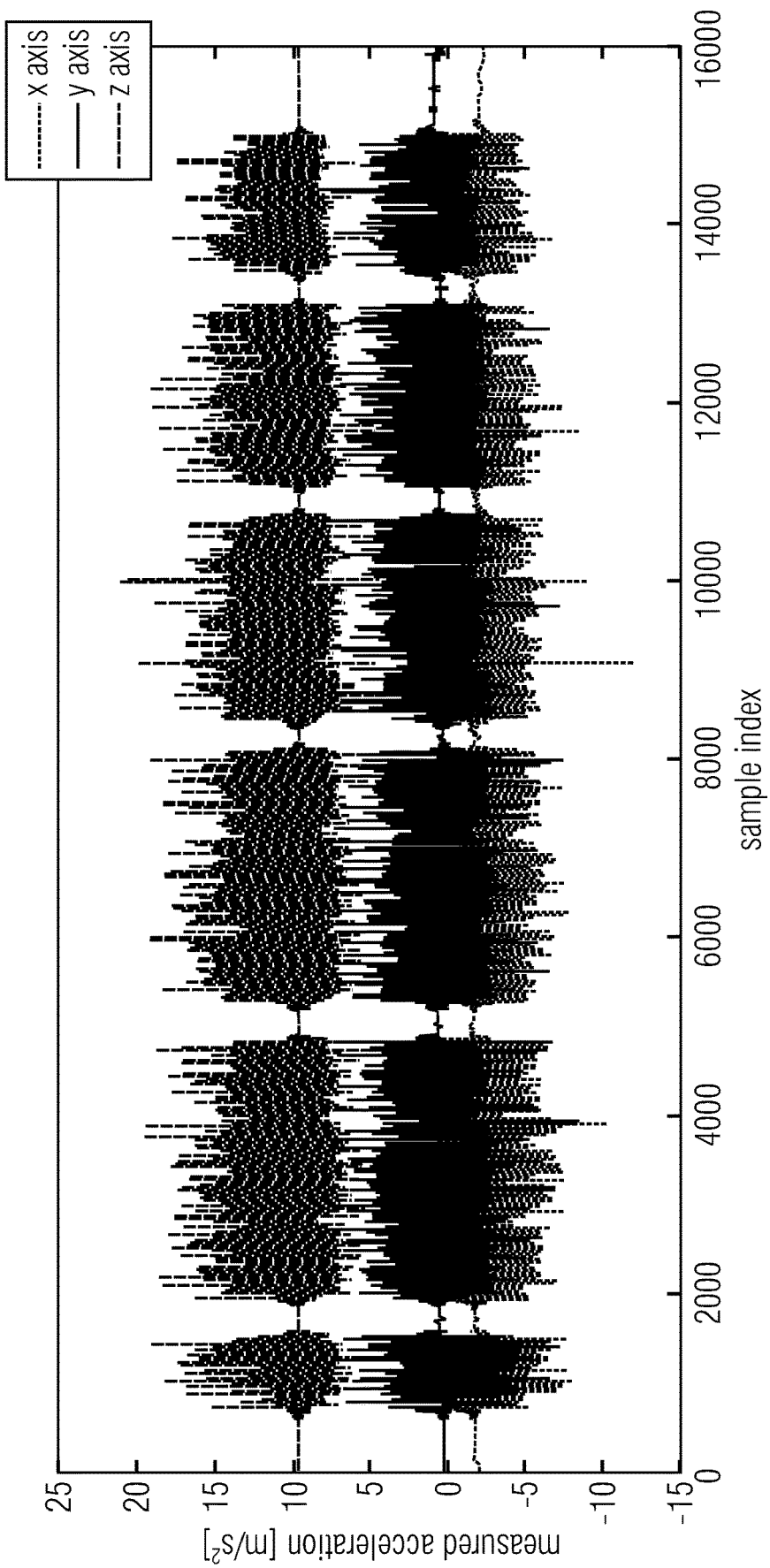
FIG. 7 shows an exemplary 3-axis accelerometer measurement of a walking pedestrian.
Figure 8:
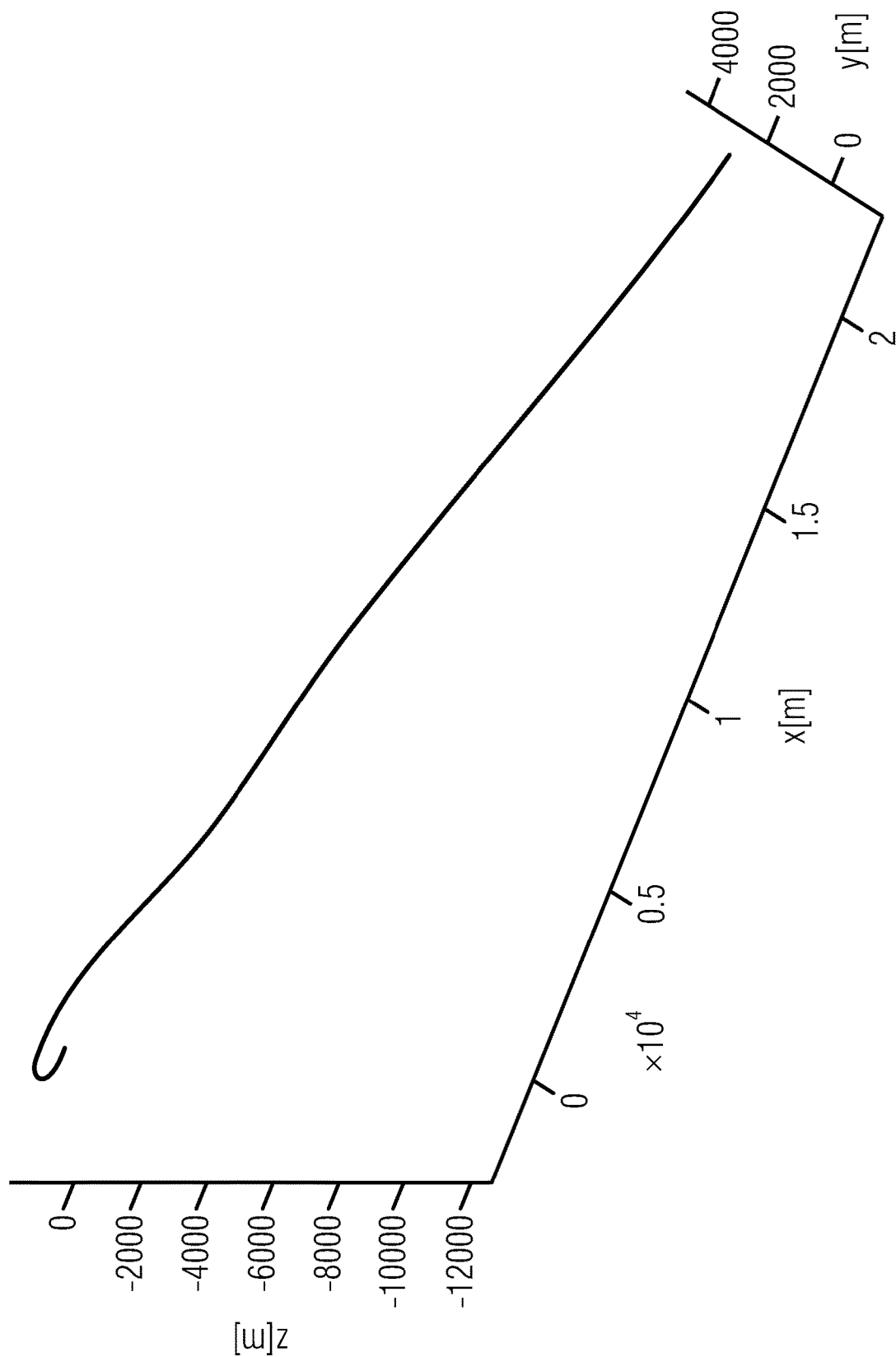
FIG. 8 shows a positioning result using classical inertial navigation.
Figure 9:
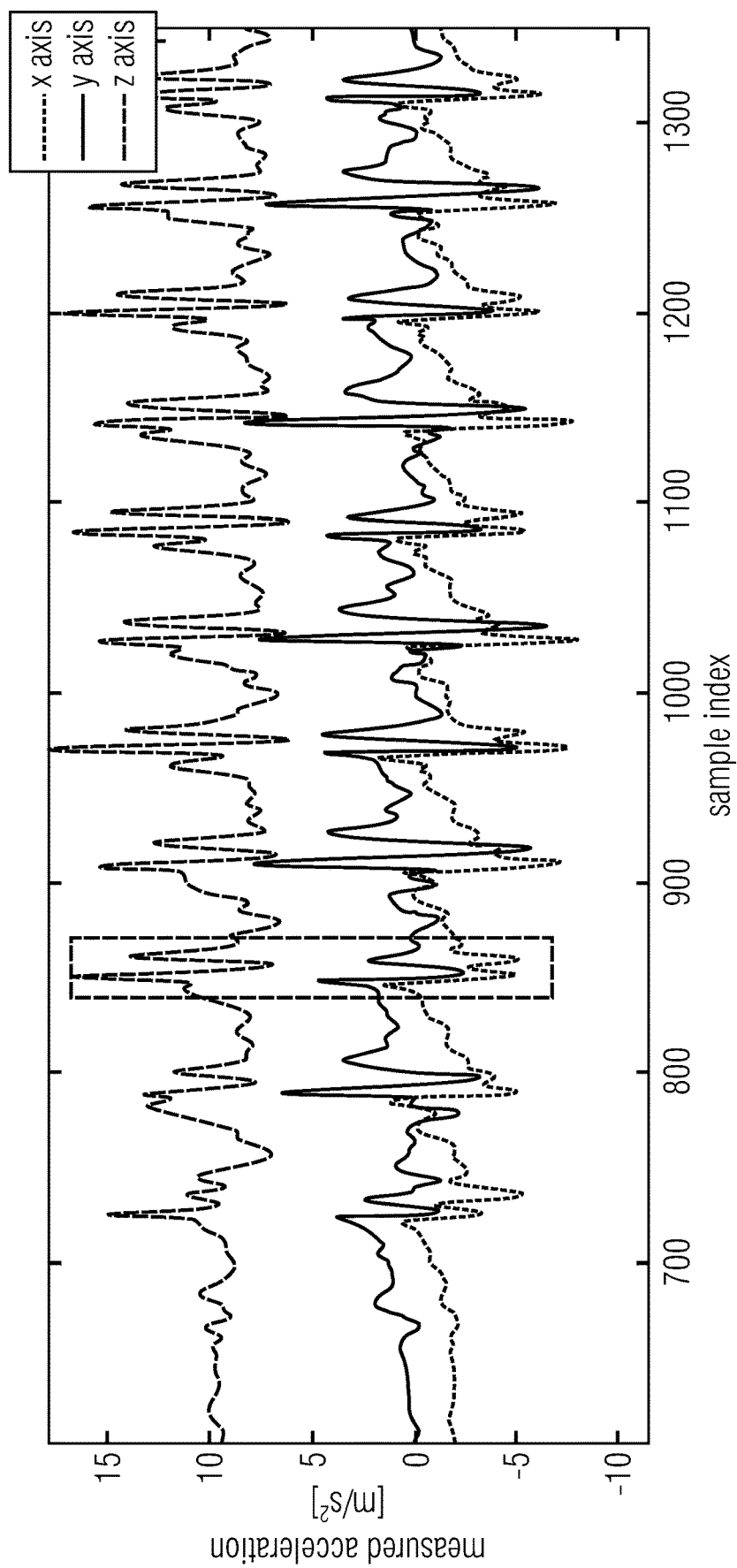
FIG. 9 shows an enlarged view of a portion of the exemplary sensor data of FIG. 7 revealing periodic peaks corresponding to the steps of the pedestrian, with an exemplary one marked by a black square.
Figure 10:
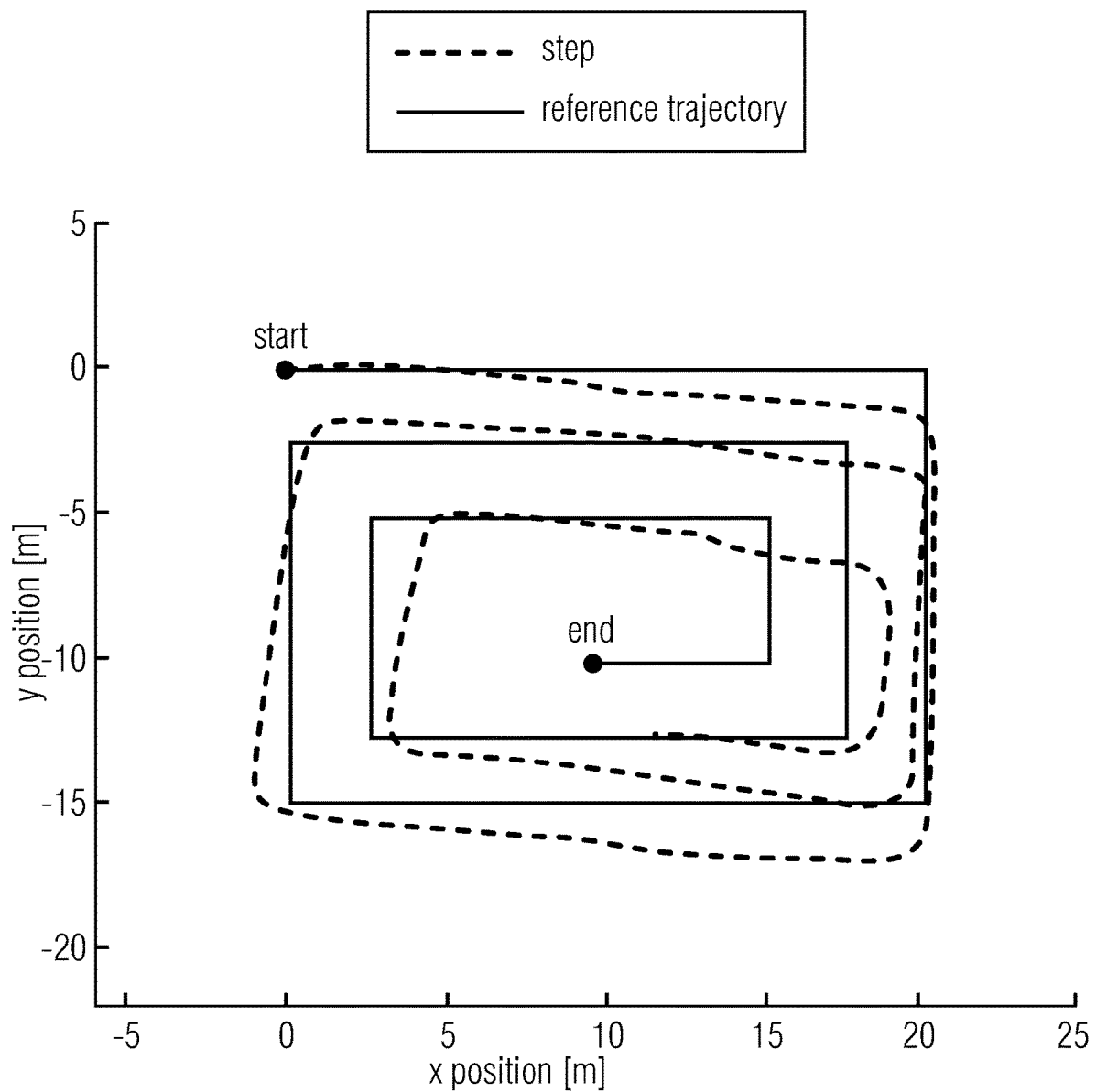
FIG. 10 shows an example of a positioning result using a movement model based approach.

Referring to FIGS. 7 to 10 an example of IMU data of a pedestrian using applying a movement model is shortly explained, wherein steps of the pedestrian are recognized. While, for some cases, classical inertial navigation (i.e., rotating the accelerometer measurements and subtracting the force of gravity to obtain the objects acceleration, which is then integrated to obtain velocity and displacement) is applicable, especially when the object uses a high-grade IMU many movement types are too dynamic to create sensor signals that can be used to obtain meaningful estimates of the velocity, attitude (orientation) and displacement. It is therefore a common practice to use movement models to extract localization information from the IMU data. To highlight this, an exemplary scenario is shown in FIGS. 7 to 10. An IMU measurement of a walking pedestrian obtained with a 3-axis accelerometer measurement is shown in FIG. 7, which shows a highly non steady signal. Using the IMU data, an inertial navigation result (other terms are strapdown navigation or INS) is obtained and shown in FIG. 8. Due to the highly dynamic behavior of the signal, a satisfying result cannot be obtained, instead the estimated position is of by kilometers at the end of the navigation scenario. When the signal from FIG. 7 is analyzed in more detail, the steps of the pedestrian can be found in the signal, as shown in FIG. 9. If, as an alternative approach, the steps are detected and used to obtain a positioning estimate, a much better result, as shown in FIG. 10 can be obtained.

Figure 11:
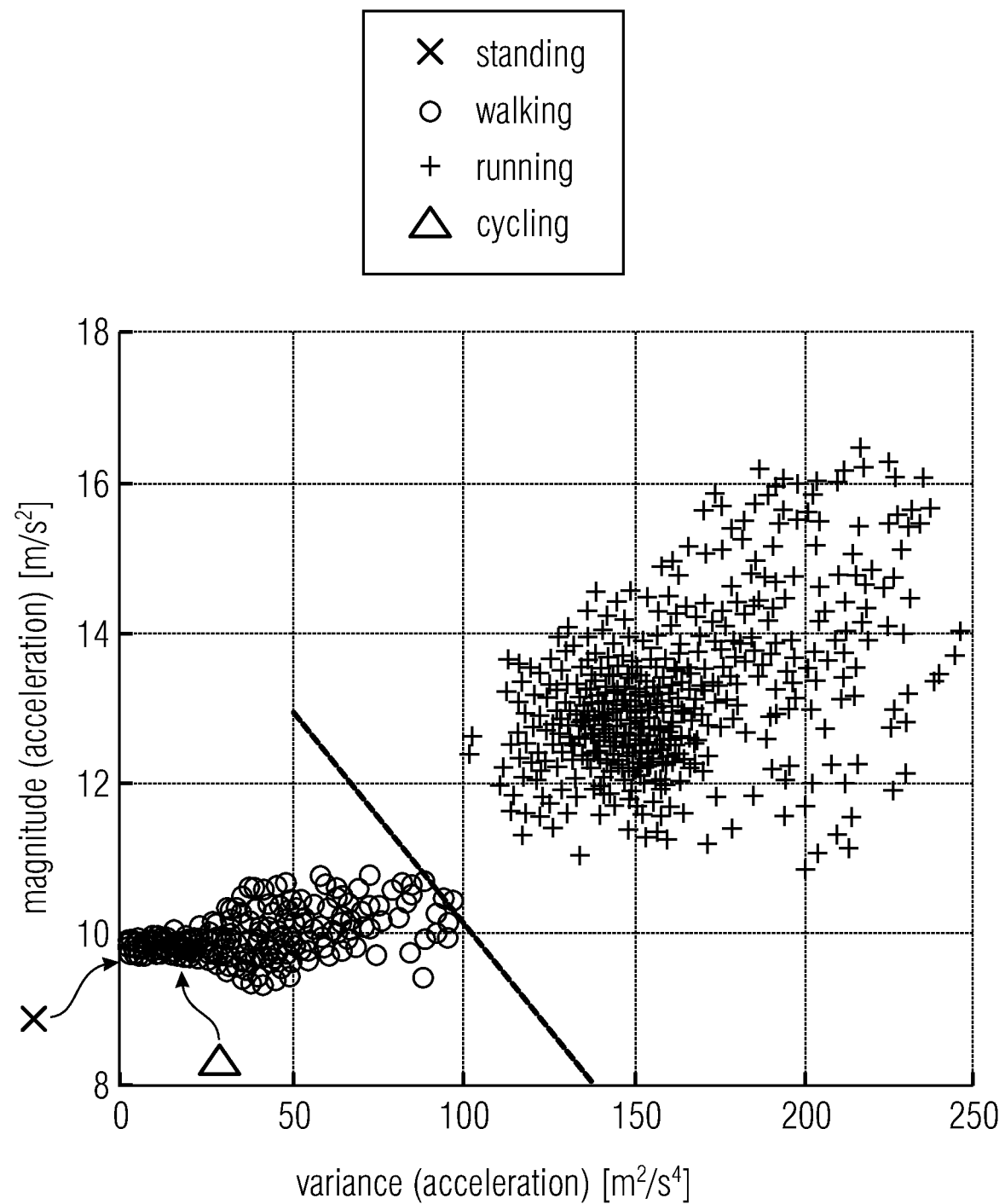
FIG. 11 shows an exemplary movement state classification using accelerometer data.

FIG. 11 shows an example of how information from other information sources may support in the identification of a motion state and, therefore, a movement model. FIG. 11 shows features obtained from accelerometer data. As can be seen features obtained from walking and cycling strongly overlap. Thus, using features obtained from the accelerometer data (namely the magnitude and variance), running can be separated from cycling and walking, but walking and cycling cannot be separated. If the velocity is used as an additional feature, the separation could be implemented easily, as a walking pedestrian moves much slower than a cyclist.

Thus, as explained above, examples of the present disclosure utilize the fact that, apart from IMU data, additional sources of information on the movement state are available in the 5G context. These include (but are not limited to) the UE type (e.g. a car cannot walk), the physical states (e.g. a smartphone moving at 50 km/h is unlikely to be held by a pedestrian), the logical position (e.g. the user of a smartphone is unlikely to drive a car within a building) and other sensors. All relevant information can be used as features in a classification approach as described herein.

Examples of the present disclosure permit an improved classification of movement states in a communication system such as LTE or 5G by using information from additional information sources beside information stemming from usual sensors. Transmitting the data as (weighted) probability mass functions over relevant movement models it is possible to link (combine) the probability mass functions from different information sources in such a manner that differences in terms of reliability of the information sources may be observed. The classified movement models may be used to support localization in order to achieve an improved result of the localization in terms of availability, robustness and precision.

In the following, additional embodiments and aspects of the invention will be described which can be used individually or in combination with any of the features and functionalities and details described herein.

According to a first aspect, an apparatus for estimating a physical state of a movable object comprises
a processor, wherein the processor is configured to
receive or determine a probability mass function including probabilities for each movement class of a first group of at least two movement classes, wherein the movement classes of the first group being determined using sensor data from the inertial measurement unit,
receive at least one additional probability mass function associated with a second group of at least two movement classes, wherein the additional probability mass function has been obtained using additional information different from the sensor data;
combine the probability mass function and the at least one additional probability mass function to obtain a combined probability mass function over the movement classes of the first group and the second group;
select a movement class having the highest probability from the combined probability mass function; and
estimate the physical state of the movable object using a movement model of the selected movement class,
wherein each movement class is either a movement state or a movement model.

According to a second aspect when referring back to the first aspect, sensor data additionally include data obtained from at least one of a magnetometer, a barometer, a temperature sensor, a microphone, a GPS receiver, a wireless local area network receiver, and a Bluetooth receiver.

According to a third aspect when referring back to the first or second aspect, the additional information concern at least one of the type of the movable object, a physical state of the movable object, a logical location of the movable object, a user behavior, a history of a user behavior, an environment of the movable object.

According to a fourth aspect when referring back to the first to third aspects, the processor is configured to obtain one or more quality measures each indicating a quality of one the probability mass functions, and wherein the processor is configured to use the quality measure in combining the probability mass function and the additional probability mass function such that a probability mass function having a higher quality is weighted higher than a probability mass function having a lower quality.

According to a fifth aspect, an apparatus for estimating a physical state of a movable object comprises
a processor, wherein the processor is configured to
receive at least one probability mass function including probabilities for each movement class of a group of at least two movement classes, wherein the probability mass function is based on information from an information source;
receive a quality measure for the probability mass function, the quality measure indicating a quality of the information source;
select a movement class having the highest probability from the at least one probability mass function, and
estimate the physical state of the movable object using a movement model of the selected movement class and the received quality measure,
wherein each movement class is either a movement state or a movement model.

According to a sixth aspect when referring to back to the fifth aspect, the at least one probability mass function is based on information from an inertial measurement unit.

According to a seventh aspect when referring to back to the fifth or sixth aspect, the processor is configured to estimate the physical state to reveal a variance of the physical state, wherein the variance depends on the quality measure, wherein a larger variance is achieved for a lower quality measure and a smaller variance is achieved for higher quality measures.

According to an eighth aspect when referring to back to the fifth or sixth aspect,
the processor is configured to
receive a plurality of probability mass functions, each comprising probabilities associated with a group of at least two movement classes, wherein each probability mass function is based on information from a different information source;
receive a quality measure for one or more of the probability mass functions,
combine the probability mass functions using the one or more quality measures such that a probability mass function having a higher quality is weighted higher than a probability mass function having a lower quality to obtain a combined probability mass function; and
select the movement class having the highest probability from the combined probability mass function.

According to a ninth aspect when referring to back to the fourth or eighth aspect, the processor is configured to combine the probability mass functions by calculating a weighted normalized sum of the probability mass functions.

According to a tenth aspect when referring to back to the fourth to ninth aspects, the processor is configured to receive each quality measure from an entity different of the movable object.

According to an eleventh aspect when referring to back to the fourth to tenth aspects, at least one of the quality measures depends on at least one of the type of the movable object and the type of the information source.

According to a twelfth aspect, a system comprises an apparatus according to one of the first to eleventh aspects and at least one information source, wherein the at least one information source is configured to transmit the probability mass function, the additional probability mass function or the at least one additional probability mass function to the apparatus.

According to a thirteenth aspect, a method for estimating a physical state of a movable object, the movable object comprising an inertial measurement unit, comprises:
receiving a probability mass function including probabilities for each movement class of a first group of at least two movement classes, wherein the movement classes of the first group being determined using sensor data from the inertial measurement unit;
receiving at least one additional probability mass function associated with a second group of at least two movement classes, wherein the additional probability mass function has been obtained using additional information different from the sensor data;
combining the probability mass function and the additional probability mass function to obtain a combined probability mass function over the movement classes of the first group and the second group;
selecting a movement class having the highest probability from the combined probability mass function; and
estimating the physical state of the movable object using a movement model of the selected movement class, wherein each movement class is either a movement state or a movement model.

According to a fourteenth aspect when referring back to the thirteenth aspect, sensor data additionally include data obtained from at least of a magnetometer, a barometer, a temperature sensor, a microphone, a GPS receiver, a wireless local area network receiver, and a Bluetooth receiver.

According to a fifteenth aspect when referring back to the thirteenth or fourteenth aspect, wherein the additional information concern at least one of the type of the movable object, a physical state of the movable object, a logical location of the movable object, a user behavior, a history of a user behavior, an environment of the movable object.

According to a sixteenth aspect when referring back to the thirteenth to fifteenth aspects, the method further comprises:
receiving one or more quality measures each indicating a quality of one the probability mass functions, wherein the quality measure is used in combining the probability mass function and the additional probability mass function such that a probability mass function having a higher quality is weighted higher than a probability mass function having a lower quality.

According to a seventeenth aspect, a method for estimating a physical state of a movable object comprises:
receiving at least one probability mass function comprising probabilities associated with a group of at least two movement classes, wherein the probability mass function is based on information from an information source;
selecting a movement class having the highest probability from the at least one probability mass function;
receiving a quality measure for the probability mass function, the quality measure indicating a quality of the information source; and
estimating the physical state of the movable object using a movement model of the selected moving class and the received quality measure,
wherein each movement class is either a movement state or a movement model.

According to an eighteenth aspect when referring back to the seventeenth aspect, the at least one probability mass function is based on information from an inertial measurement unit.

According to a nineteenth aspect when referring back to the seventeenth or eighteenth aspect, estimating the physical state reveals a variance of the physical state, wherein the variance depends on the quality measure, wherein a larger variance is achieved for a lower quality measure and a smaller variance is achieved for higher quality measures.

According to a twentieth aspect when referring back to the seventeenth or eighteenth aspect,
a plurality of probability mass functions is received, each comprising probabilities associated with a group of at least two movement classes, wherein each probability mass function is based on information from a different information source,
wherein a quality measure is received for one or more of the probability mass functions,
wherein the probability mass functions are combined using the one or more quality measures such that a probability mass function having a higher quality is weighted higher than a probability mass function having a lower quality to obtain a combined probability mass function, and
wherein the movement class having the highest probability is selected from the combined probability mass function.

According to a twenty-first aspect when referring back to the sixteenth or twentieth aspect, combining the probability mass functions comprises calculating a weighted normalized sum of the probability mass functions.

According to a twenty-second aspect when referring back to the sixteenth to twenty-first aspects, each quality measure is received from an entity different of the movable object.

According to a twenty-third aspect when referring back to the sixteenth to twenty-second aspects, at least one of the quality measures depends on at least one of the type of the movable object and the type of the information source.

According to a twenty-fourth aspect when referring back to the thirteenth to twenty-third aspects, the method further comprises transmitting the probability mass function, the additional probability mass function or the at least one additional probability mass function via a radio communication link.

According to a twenty-fifth aspect, a non-transitory computer program product comprises a computer readable medium storing instructions which, when executed on a computer, perform the method according to the thirteenth to twenty-fourth aspects.

Although some aspects of the described concept have been described in the context of an apparatus, it is clear that these aspects also represent a description of the corresponding method, where a block or a device corresponds to a method step or a feature of a method step. Analogously, aspects described in the context of a method step also represent a description of a corresponding block or item or feature of a corresponding apparatus.

The terms "computer program medium" and "computer readable medium" are used to generally refer to tangible storage media such as removable storage units or a hard disk installed in a hard disk drive. These computer program products are means for providing software to a computer system. The computer programs, also referred to as computer control logic, may be stored in a main memory and/or a secondary memory. Computer programs may also be received via a communications interface. The computer program, when executed, enable the computer system to implement the present invention. In particular, the computer program, when executed, enable the processor to implement the processes of the present invention, such as any of the methods described herein. Accordingly, such a computer program may represent a controller of the computer system. Where the disclosure is implemented using software, the software may be stored in a computer program product and loaded into computer system using a removable storage drive or a communications interface.

The implementation in hardware or in software may be performed using a digital storage medium, for example cloud storage, a floppy disk, a DVD, a Blue-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention may be implemented as a computer program product with a program code, the program code being operative for performing one of the methods when the computer program product runs on a computer. The program code may be stored on a machine readable carrier, for example.

Other embodiments comprise the computer program for performing one of the methods described herein, stored on a machine readable carrier. In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. A further embodiment of the inventive method is, therefore, a data stream or a sequence of signals representing the computer program for performing one of the methods described herein. The data stream or the sequence of signals may for example be configured to be transferred via a data communication connection, for example via the Internet. A further embodiment comprises a processing means, for example a computer, or a programmable logic device, configured to or adapted to perform one of the methods described herein. A further embodiment comprises a computer having installed thereon the computer program for performing one of the methods described herein.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are performed by any hardware apparatus.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for estimating a physical state of a movable object, the apparatus comprising a processor, wherein the processor is configured to receive or determine a probability mass function comprising probabilities for each movement class of a first group of at least two movement classes, wherein the movement classes of the first group being determined using sensor data from the inertial measurement unit of the movable object;
   receive at least one additional probability mass function associated with a second group of at least two movement classes, wherein the additional probability mass function has been acquired using additional information different from the sensor data; combine the probability mass function and the at least one additional probability mass function to acquire a combined probability mass function over the movement classes of the first group and the second group;
   select a movement class comprising the highest probability from the combined probability mass function; and
   estimate the physical state of the movable object using a movement model of the selected movement class, wherein each movement class is either a movement state or a movement model, and wherein the additional information different from the sensor data concerns information from other devices in the vicinity of the object determined via device to device (D2D) data exchanged directly with the other devices.

2. The apparatus of claim 1, wherein sensor data additionally comprise data acquired from at least one of a magnetometer, a barometer, a temperature sensor, a microphone, a GPS receiver, a wireless local area network receiver, and a Bluetooth receiver.

3. The apparatus of claim 1, wherein the processor is configured to acquire one or more quality measures each indicating a quality of one the probability mass functions, and wherein the processor is configured to use the quality measure in combining the probability mass function and the additional probability mass function such that a probability mass function comprising a higher quality is weighted higher than a probability mass function comprising a lower quality.

4. The apparatus of claim 3, wherein the processor is configured to estimate the physical state to reveal a variance of the physical state, wherein the variance depends on the quality measure, wherein a larger variance is achieved for a lower quality measure and a smaller variance is achieved for higher quality measures.

5. The apparatus of claim 3, wherein the processor is configured to combine the probability mass functions by calculating a weighted normalized sum of the probability mass functions.

6. The apparatus of claim 3, wherein the processor is configured to receive each quality measure from an entity different of the movable object.

7. The apparatus of claim 3, wherein at least one of the quality measures depends on at least one of the type of the movable object and the type of the information source.

8. A system comprising an apparatus for estimating a physical state of a movable object, the apparatus comprising a processor, wherein the processor is configured to receive or determine a probability mass function comprising probabilities for each movement class of a first group of at least two movement classes, wherein the movement classes of the first group being determined using sensor data from the inertial measurement unit, receive at least one additional probability mass function associated with a second group of at least two movement classes, wherein the additional probability mass function has been acquired using additional information different from the sensor data; combine the probability mass function and the at least one additional probability mass function to acquire a combined probability mass function over the movement classes of the first group and the second group; select a movement class comprising the highest probability from the combined probability mass function; and estimate the physical state of the movable object using a movement model of the selected movement class, wherein each movement class is either a movement state or a movement model, and wherein the additional information different from the sensor data concerns information from other devices in the vicinity of the object determined via device to device (D2D) data exchanged directly with the other devices; and at least one information source, wherein the at least one information source is configured to transmit the probability mass function, the additional probability mass function or the at least one additional probability mass function to the apparatus.

9. A method for estimating a physical state of a movable object, the movable object comprising an inertial measurement unit, the method comprising: receiving a probability mass function comprising probabilities for each movement class of a first group of at least two movement classes, wherein the movement classes of the first group being determined using sensor data from the inertial measurement unit; receiving at least one additional probability mass function associated with a second group of at least two movement classes, wherein the additional probability mass function has been acquired using additional information different from the sensor data; combining the probability mass function and the additional probability mass function to acquire a combined probability mass function over the movement classes of the first group and the second group; selecting a movement class comprising the highest probability from the combined probability mass function; and
estimating the physical state of the movable object using a movement model of the selected movement class, wherein each movement class is either a movement state or a movement model, and wherein the additional information different from the sensor data concerns information from other devices in the vicinity of the object determined via device to device (D2D) data exchanged directly with the other devices.

10. The method of claim 9, wherein sensor data additionally comprise data acquired from at least of a magnetometer, a barometer, a temperature sensor, a microphone, a GPS receiver, a wireless local area network receiver, and a Bluetooth receiver.

11. The method of claim 9, further comprising transmitting the probability mass function, the additional probability mass function or the at least one additional probability mass function via a radio communication link.

12. The method of claim 9, further comprising: receiving one or more quality measures each indicating a quality of one the probability mass functions, wherein the quality measure is used in combining the probability mass function and the additional probability mass function such that a probability mass function comprising a higher quality is weighted higher than a probability mass function comprising a lower quality.

13. The method of claim 12, wherein estimating the physical state reveals a variance of the physical state, wherein the variance depends on the quality measure, wherein a larger variance is achieved for a lower quality measure and a smaller variance is achieved for higher quality measures.

14. The method of claim 12, wherein combining the probability mass functions comprises calculating a weighted normalized sum of the probability mass functions.

15. The method of claim 12, wherein each quality measure is received from an entity different of the movable object.

16. The method of claim 12, wherein at least one of the quality measures depends on at least one of the type of the movable object and the type of the information source.

17. A non-transitory digital storage medium having a computer program stored thereon to perform the method for estimating a physical state of a movable object, the movable object comprising an inertial measurement unit, the method comprising: receiving a probability mass function comprising probabilities for each movement class of a first group of at least two movement classes, wherein the movement classes of the first group being determined using sensor data from the inertial measurement unit; receiving at least one additional probability mass function associated with a second group of at least two movement classes, wherein the additional probability mass function has been acquired using additional information different from the sensor data; combining the probability mass function and the additional probability mass function to acquire a combined probability mass function over the movement classes of the first group and the second group; selecting a movement class comprising the highest probability from the combined probability mass function; and estimating the physical state of the movable object using a movement model of the selected movement class, wherein each movement class is either a movement state or a movement model, and wherein the additional information different from the sensor data concerns information from other devices in the vicinity of the object determined via device to device (D2D) data exchanged directly with the other devices, when said computer program is run by a computer.

\* \* \* \* \*